United States Patent [19]

Frabricius et al.

[11] 4,390,623
[45] Jun. 28, 1983

[54] SERUM-FREE AND MITOGEN-FREE T-CELL GROWTH FACTOR AND PROCESS FOR MAKING SAME

[75] Inventors: Hans-Ake Frabricius, Breisach; Roland Stahn, Holzhausen, both of Fed. Rep. of Germany

[73] Assignee: Hooper Trading Company, Curacao, Netherlands Antilles

[21] Appl. No.: 247,769

[22] Filed: Mar. 26, 1981

Related U.S. Application Data

[63] Continuation-in-part of Ser. No. 193,112, Oct. 2, 1980, abandoned.

[51] Int. Cl.³ .................................... C12P 21/00
[52] U.S. Cl. ................................. 435/68; 435/948; 435/240; 435/284
[58] Field of Search ............... 424/95, 101; 435/68

[56] References Cited

U.S. PATENT DOCUMENTS 3,800,035  3/1974  Moshe Goore ................ 435/68

OTHER PUBLICATIONS

Mochizuki et al.–J. of Immunology, vol. 125, Dec. 1980, pp. 2579–2583.
Bodeker–Eur. J. Immunol., vol. 10, 1980, pp. 702–707.
Christopher S. Henney, et al. Nature, 291, pp. 335–338 (May 28, 1982).
K. Kuribayashi, et al. J. of Immunology, 126, No. 6, pp. 2321–2327 (Jun. 1981).
K. Nagy-Vezekenyi, et al., A. Hautr, 55 (24): 1630–1636 (Apr. 1980) (German with English Translation).
Papermaster, et al. Clinical Immunology and Immunopathology 5, 31–47 (1976).
Mills, et al. J. of Immunology, vol. 125, No. 5, pp. 1904–1909 (Nov. 1980).
Lotze, et al. J. of Immunology 125: 4, pp. 1487–1493 (Oct. 1980).
Wagner, et al. Immunological Rev. 51, pp. 215–255 (1980) (pp. 215 and 221 only).
Paetkau Nature 294: 24, pp. 689–690 (Dec. 31, 1981).
Needleman, et al. J. of Immunological Methods, 44, pp. 3–14 (1981).
Warren, et al. J. Of Immunological Methods, 41, pp. 9–21 (1981).
Farrar, et al. J. of Immunology, 125: N, pp. 793–798 (Aug. 1980).
Shaw, et al. J. of Immunology, 124: 5, pp. 2231–2239 (May 1980).
Gillis, et al. J. of Immunology, 125: 6, pp. 2570–2578 (Dec. 1980).
Rosenberg, et al. J. of Immunological Methods, 33, pp. 337–350 (1980).
Watson, et al. Immunology Today, pp. 113–116 (Dec. 1980).
Paetkau, et al. Immunological Reviews, vol. 51, pp. 157–175.
Sanderson, et al. Immunological Reviews, vol. 51, pp. 177–191.
Watson, et al. Immunological Reviews, vol. 51, pp. 257–278.
Smith Immunological Reviews, vol. 51, pp. 337–357.
Mills, et al. J. of Immunology, 125: 5, pp. 1897–1903 (Nov. 1980).
Herberman, et al. J. Nat'l. Cancer Inst., 62: 3, pp. 441–445 (Mar. 1979).
Herberman, et al. Science, 214, pp. 24–30 (Oct. 1981).
Beverley Nature, 280, p. 362 (Aug. 23, 1979).
Fabricius, et al. Immunobiol., 156, pp. 364–371 (1979).
Lucas, et al. Regulatory Mechanisms in Lymphocyte Activation, pp. 76–93.
Alvarez, et al. J. of Immunology, 123, No. 3, pp. 977–984 (1979).
Gillis, et al., J. of Immunology 120, p. 2027–2033 (1978).
Fagnani, et al., J. of Immunological Methods, 33, pp. 313–322, 1980.

*Primary Examiner*—Sam Rosen
*Attorney, Agent, or Firm*—Sherman & Shalloway

[57] ABSTRACT

A serum-free and mitogen-free T-cell growth factor (interleukin-2) preparation is prepared from human, bovine, or procine peripheral mononuclear blood cells which are washed several times with a liquid tissue culture medium and then stimulated in a tissue culture medium supplemented with serum and mitogen. The separated stimulated cells are again washed with fresh tissue culture medium to remove substantially all of the serum and mitogen. The washed cells are suspended in fresh tissue culture medium and conditioned under incubation conditions to transfer the growth factor into the liquid. The tissue culture medium separated from the stimulated cells can be recycled to stimulate additional cells. The supernatant can be concentrated from 50 to 100-fold on an ultrafilter. The supernatant can activate the production of natural killer cells in patients suffering from tumors.

13 Claims, 5 Drawing Figures

SERUM-FREE AND MITOGEN-FREE T-CELL GROWTH FACTOR AND PROCESS FOR MAKING SAME

This application is a continuation-in-part of application Ser. No. 193,112 filed Oct. 2, 1980, now abandoned.

BACKGROUND

This invention is directed to a serum-free and mitogen-free growth factor for thymus-derived lumphocyte (i.e., T-cell growth factor) and a process of producing same. This invention is also directed to the use of the above-mentioned T-cell growth factor in the treatment of patients suffering from tumors and in improving the growth of natural killer cells in such patients.

T-cell growth factor (TCGF), also referred to as Interleukin 2 (IL 2) is a protein which functions to activate blastogenesis and the proliferation of cytotoxic lymphocytes dependent on the thymus (T-cells). Hereinafter, T-cell growth factor (TCGF) and Interleukin 2 (IL 2) will be used interchangeably to designate the same material. IL 2 is defined by its ability to support growth of T-lymphocyte lines in cell cultures. IL 2 activates a subpopulation of T-cells which is distinguished by specific cytotoxic properties and natural killer properties. "Natural killing" refers to the ability of such cells to kill tumor cells without previous sensitizing. These cells represent the most important effector cells in the immune reactions against spontaneous malignant tumors. Natural killer cells are important since they represent the first line of defense in the body against tumors. It has been found that the activity of natural killer cells in tumor patients is suppressed. Therefore, when the natural killer cells in the patient are stimulated into activity, the growth of the tumor cells can be stopped.

In addition, it has been suggested that IL 2 may be used in the defense against viral deseases. Furthermore, a decisive role has been attributed to IL 2 in the rejection of transplants. By suppressing the production of IL 2 in the patient after a transplantation operation, the probability of the patient rejecting the transplant is substantially decreased.

As mentioned above, tumor patients have been found to be defective in the function of the cellular immune system attributable to a defect in the in vitro ability to produce IL 2. If it is assumed that the tumor causes and must cause this defect in order to survive, a therapeutic procedure can be established by supplying the patient with preparations containing IL 2 in order to activate the inactive natural killer cells.

Such a therapeutic procedure is similar to that for interferon. Recently, most interest has been directed to the effect of interferon on cancer. Interferon is known to be effective in killing virus-infected cells, although its effect on cancer is still unknown. It is of interest to note that it is species specific, i.e., interferon, to be effective on humans, must be extracted from human blood. On the other hand, IL 2 produced with cells from bovine blood and spleen has been found to activate human cells. This also applies to porcine blood and spleen. However, IL 2 extracted from mice or rats will not activate human cells since the donor belongs to a species which is too biologically unrelated to humans. IL 2 extracted from large animals such as cows, pigs and sheep will activate human cells. This is significant in that with IL 2, the risk of introducing into the patient hepatitis virus carried in the donor's blood can be avoided by using bovine (cattle) or porcine (pig) lymphocytes. Another advantage is that the supply of bovine and porcine lymphocytes is much greater than that of human cells.

According to Lucas, et al., "Parameters of Lymphocyte Activation," IL 2 is not identical to interferon but occurs in stimulated leucocyte supernatants containing interferon. Possibly, part of the therapeutic effect of leucocyte interferon preparations is due to the IL 2 contained therein.

The production of IL 2 has been discussed by Alvarez, et al., "Human T-Cell Growth Factor," *J. of Immunology*, 123, 3, 977 (1979) and Gillis, et al., "T-cell growth factor: parameters of production and quantitative microassay for activity," *J. of Immunology*, 120, 2027 (1978). In general, IL 2 is produced by stimulating peripheral mononuclear blood cells with a mitogen or antigen.

The production of a phytohemagglutinin-(PHA)-free T-cell growth factor is discussed in Fagani, et al., "Removal of PHA from conditioned medium by affinity chromatography," *J. of Immunological Methods*, 33, 313 (1980). The procedure described therein is not only cumbersome but also provides a product which contains serum. The presence of serum which contains numerous proteins may mask the true effect of IL 2 and repeated injections of such a serum-containing preparation regularly cause allergic and anaphylactic reactions in patients. Furthermore, a serum-containing IL 2 cannot be concentrated since the serum will precipitate and plug the pores in the filter.

The present inventors have successfully produced serum-free and mitogen-free T-cell growth factor. Heretofore, it has been accepted that serum is necessary for cell growth. As a result, serum is always used in cell culture. Through serum-free production, the present growth factor can be highly concentrated and the activity thereof can be increased between 300 and 500 times. Furthermore, since no toxic substances, such as lectins, for example, are present in the growth factor, the cells from which the growth factor is extracted can be used several times before losing its activity. As a result, the efficiency of the extraction process is substantially improved over the prior art. Thus, the present invention is believed to provide a clear and significant advance in the art.

SUMMARY OF THE INVENTION

According to the present invention, a serum-free mitogen-free T-cell growth factor is provided. The growth factor is obtained by isolating peripheral mononuclear blood cells from the blood or the spleen of a donor; stimulating the cells in the presence of a tissue culture medium supplemented with serum and a mitogen; washing the stimulated cells free of the serum and mitogen; and conditioning the cells to transfer the growth factor from the cells to the liquid phase of the tissue culture medium.

The serum-free and mitogen-free T-cell growth factor can be used to stimulate the growth of natural killer cells in tumor patients to prevent the growth of or eliminate the tumor cells.

DETAILED DESCRIPTION OF THE INVENTION

According to the present invention, a T-cell (thymus derived lymphocyte) growth factor (TCGF) which is free of serum and mitogen is provided. To prepare the novel TCGF, the following processes, all performed under sterile conditions, may be used.

In a first embodiment, blood is withdrawn from a donor. As donor, cattle, pigs and humans may be used. The T-cell growth factor of the present invention is not species specific. Accordingly, growth factor extracts from bovine or porcine blood can be administered to human patients. In view of the fact that human blood is very much limited in supply and has the risk of being a carrier of hepatitis, bovine (cattle) and porcine (pig) blood are preferred. The withdrawn blood is mixed with an anti-coagulant such as Heparin. Peripheral mononuclear blood cells are isolated from the blood using methods known in the art. As an example of a useful isolation method, the blood is layered into a tube containing a high density polymeric solution, commercially available as Ficoll-hypaque, and centrifuged. Peripheral mononuclear blood cells are collected above the polymeric solution and are carefully removed. Since the Ficoll-hypaque solution is slightly toxic, the removal must be done with great caution. The so-obtained peripheral mononuclear blood cells are washed several times, usually three, with a sterile solution to ensure the complete removal of the Ficoll-hypaque solution. By washing, it is meant that the cells are gently suspended in the sterile solution and centrifuged to separate the cells again from the solution. Low centrifuge speed and time are used (e.g., 300 G for ten minutes) in order to avoid breakage or destruction of the cells. A useful sterile solution for washing the cells is the formulation Roswell Park Memorial Institute (RPMI) 1640 which is commercially available. After centrifugation, the supernatant is discarded and a fresh portion of the sterile solution is added thereto. The washing is then repeated. The cells are then ready for further processing. It should be noted that machines are presently available for the automatic separation of mononuclear cells from blood which greatly reduces the time for such separation.

Alternatively, the spleen from cattle, pigs or humans can be used in place of blood as a very rich source for the mononuclear cells. Methods for separating the mononuclear cells from the spleen are known in the art. Generally, the spleen is minced in a sterile saline solution and then passed through a stainless steel mesh. The so-obtained suspension containing the mononuclear cells is then treated to extract the cells therefrom in accordance with the procedure given above for blood. By extracting the mononuclear cells from the spleen, a larger amount of the cells is obtained. Typically, 2 to $10 \times 10^{12}$ cells can be collected from the donor's blood.

As an example, the spleen is removed from a donor. Thereafter, it is minced in a sterile saline solution (e.g., Hank's Balanced Salt Solution which is readily available commercially) into pieces of approximately 1 mm size and forced through a stainless steel mesh having a mesh size of about 0.1 mm. Such stainless steel mesh is readily available commercially. The cells-containing suspension so-obtained can then be layered onto Ficoll-hypaque gradients to extract the mononuclear cells, as described above. Usually, several grams of cells are obtained (one gram contains about $10^{12}$ cells).

In the next step, the mononuclear cells are subjected to stimulation with a mitogen. In this step, the cells are suspended in a tissue culture medium supplemented with serum and a mitogen and incubated for a suitable period of time. A useful tissue culture medium is RPMI 1640. The RPMI 1640 is supplemented with 15% vol/vol human AB serum and 4 micrograms of a mitogen per ml or RPMI 1640. A particularly preferred mitogen in the present invention is phytohemagglutinin (PHA). Other useful mitogens include concanavalin A (Con A), Escherichia coli lipopolysaccharide (LPS), and pokeweed mitogen (PWM). The cell density in the suspension is adjusted to about $3 \times 10^6$ per ml of RPMI 1640. The suspension is incubated for about 4 to 12 hours at a temperature of about 37° C. in an atmosphere containing from about 5 to 10%, preferably about 7.5% carbon dioxide. Although the incubation may be conducted for 4 to 12 hours, it has been found that four hours represent the optimum time. It is noted that the experimental conditions (e.g., temperature, humidity level, amount of $CO_2$ in the atmosphere) used in this incubation step are similar to the "standard" conditions frequently used in tissue culture, such conditions being well known to those skilled in the art.

After incubation, the cells are separated from the solution by means of, for example, centrifugation. The so-obtained supernatant is decanted and held for recycling, if preferred. However, prior to use, it is preferred to filter the supernatant in order to guard against the presence of bacteria therein. The cells are washed several times in fresh portions of a tissue culture medium, such as RPMI 1640, containing no serum and no PHA, in order to remove all of the serum and mitogen present in the cell pellet. The washing procedure comprises suspending the cells in the medium and then separating the cells therefrom, as described above. It has been found that three washings (i.e., three consecutive suspendings in fresh portions of RPMI 1640 and centrifuging, with the wash solution being discarded after each washing) are sufficient to remove substantially all of the serum and mitogen. Results obtained by using a radioactive isotope tagging method clearly support that after three washings, substantially all of the serum and mitogen have been eliminated.

Furthermore, it is estimated that after three washings, the dilution factor of materials present in the cell pellet prior to washing is about $30 \times 10^6$. Accordingly, the concentration of the serum and mitogen in contact with the washed cells is reduced to near zero. After washing, the cells are suspended again in a serum-free, mitogen-free tissue culture medium, e.g., RPMI 1640, which suspension is ready for conditioning to transfer the growth factor from the cells to the liquid phase.

In the conditioning step, the suspension of cells in RPMI 1640 is incubated under standard conditions used in tissue culture for a period of from about 12 to 20 hours, preferably from about 15 to 20 hours, most preferably about 18 hours.

After conditioning by incubation, the cells are separated from the suspension by means of, for example, centrifugation. The supernatant which contains the product T-cell growth factor is collected. As to the cells, they may be restimulated with the supernatant comprising the culture medium, serum and PHA. The recycle of the supernatant and cells may be conducted up to 5 times.

The T-cell growth factor (IL 2) containing supernatant is further subjected to filtration. The filter preferably has a pore opening of from about 0.2 to 0.4 microns. This filtration step is preferably included in the present process in order to assure the production of a cell-free supernatant. The filtered supernatant may then be processed to yield a more concentrated product.

To concentrate the supernatant, the supernatant may be subjected to ultrafiltration using an ultrafilter which does not absorb protein. Since IL 2 is believed to be a protein, ultrafilters which normally absorb protein should clearly be avoided. The purpose of this concentration step is to remove small molecules such as salt, sugar and water from the supernatant. Thus, ultrafilters having a filtration range of molecular weights between 10,000 and 30,000 should be used. Particularly useful ultrafilters include YM-10 and YM-30 type ultrafilters manufactured by Amicon Co. U.S.A., since they do not absorb protein. The liquid product retained on top of the ultrafilter membrane represents the desired end product. Usually, a concentration factor of 50-fold to 250-fold may be obtained. The final product, which is in the form of a liquid, may be stored for a period of about 1 to 2 months at 4° C. and for about 1 year at −20° C. without losing its activity. Thus, there is obtained a serum-free and mitogen-free T-cell growth factor from the blood or spleen of human, bovine or porcine donors. Bovine donors can also be used.

In the above-described procedure, all of the experimental steps are conducted at room temperature, i.e., 20°–25° C., with the exception of the incubation steps. Furthermore, the entire process is conducted under sterile conditions. In this connection, where sterilized ultrafilters are not available, it will be necessary to re-sterilize the liquid product prior to use. It may also be desirable to remove the tissue culture medium from the liquid product and replace same with an infusion solution for injection into a patient.

To ascertain that the product T-cell growth factor is free of mitogen (PHA), two sets of experiments have been conducted. The first set of experiments comprises radioactive labelling of the PHA used in stimulating the cells. In a 300-fold concentrate on the resulting T-cell growth factor less than 1% of the original activity is measured. In the second set of experiments, anti-PHA antibodies are added to the product T-cell growth factor which is then subjected to microtitering. Comparison of a control sample and the sample containing the anti-PHA antibodies indicates that there is no difference in the activity of the T-cell growth factor in both samples.

To show that the product T-cell growth factor is serum-free, albumin which constitutes 50% of serum is used in the cell stimulation step of the present invention as a marker. The radial immunodiffusion method suggested by Mancini is used to determine the activity of albumin in the product T-cell growth factor. In a 300-fold concentrate of the T-cell growth factor obtained in accordance with the present invention in which albumin is used as the marker for serum, no albumin activity can be measured. Hence, the above-mentioned tests clearly establish that the present T-cell growth factor is mitogen-free and serum-free.

As has been mentioned, a serum-free T-cell growth factor is an important feature of the invention. Although the presence of serum has no effect on the activity of IL 2, a serum-free preparation involves lower risk in use. The patient may also become allergic to serum proteins. Furthermore, a serum-free T-cell growth factor can be concentrated by using an ultrafilter. Such concentration is not possible in the presence of serum since the serum will clog the pores in the filter.

In another embodiment of the present invention, an alternative method of producing T-cell growth factor is provided. This method is based on the fact that T-cells comprise T-cell growth factor producer cells which adhere to such substrates as glass, plastic and nylon, and T-cell growth factor responder cells which do not adhere to substrates. By allowing the cells to come in contact with a suitable substrate, the producer cells will adhere to the substrate and be made available for further processing to yield the desired T-cell growth factor.

In this embodiment, peripheral mononuclear blood cells are separated from the donor's blood or spleen as described above. The cells are washed repeatedly, e.g., three times with a sterile solution such as RPMI 1640. The cells which are suspended in the sterile solution are then ready for separation into an adhering portion and a non-adhering portion.

To separate the cells, the suspension is permitted to contact a suitable substrate such as glass beads, nylon wool and hollow porous fibers. The substrate may be conveniently stored in a container such as a column of suitable dimension. Since the adhesion of the producer cells to the substrate is not a rapid process, sufficient time should be allowed. Thereafter, a sterile solution such as RPMI 1640 is caused to flow over the substrate to flush out the non-adhering responder cells. After such a cell separation step, the producer cells are stimulated by adding to the container or column in which the cells and substrate are stored, a tissue culture medium, such as RPMI 1640, supplemented with human AB serum and a mitogen such as PHA. The amounts of serum and PHA added to the RPMI 1640 are identical to those described in the first method. The mixture (i.e., cells, tissue culture medium and substrate) is incubated for 4 to 12 hours, preferably 4 hours.

After incubation, the tissue culture medium is drained off and saved for stimulating another batch of peripheral mononuclear cells. The substrate and stimulated cells are washed with fresh portions of tissue culture medium containing no supplements to flush out all of the serum and mitogen.

Fresh tissue culture medium is then added to fill the container. The cells are new ready for conditioning.

To condition the cells, the substrate bearing the cells is incubated under standard conditions used in tissue culture experiments for 12 to 24 hours, preferably 15 to 20 hours, most preferably 18 hours. After incubation, the tissue culture medium containing the product is collected and fresh portions of tissue culture medium are added to wash out the formed product and are collected. The amounts of fresh tissue culture medium used to wash the substrate and cells are usually not important, the primary purpose here being to remove as much of the product as possible. The T-cell growth factor-containing tissue medium so collected may be subjected to concentration to yield a final product. The conditions used in the concentration step are identical to that mentioned above. The cell-bearing substrate can be restimulated by recycling the tissue culture medium supplemented with serum and mitogen collected previously in the first incubation/stimulation step.

By adhering the producer cells to a substrate, several advantages can be achieved. First, a much faster process is provided since no spin down or centrifuging to separate the cells is needed. Second, the washing of the cells can be made a continuous step by adjusting the feed and exit flow rates of the tissue culture medium, thus shortening the process. As a matter of fact, the only steps which may not be continuous are the two incubation steps; all the other steps can be made continuous. Third, since the substrate and cells are stored in one container, which can be stimulated and re-stimulated for several times, typically five times, the container may be made of a disposable material, with the entire container of substrate and cells being discarded after a prescribed number of times of use.

It has been mentioned that as substrates, glass beads, nylon wool, and hollow porous fibers can be used. When glass beads and nylon wood are used, they may be packed and placed in a column. Fresh tissue culture medium is fed to the column at the top and washings or product solutions are withdrawn at the bottom. The dimension of the column may be varied in accordance with the magnitude of the process. The useful diameter of the glass beads depends on the surface area desired. Usually, the bead diameter is between 20 and 100 microns and preferably should not exceed 1 mm. As an alternative, the glass beads may be in form of a bed of fritted glass. The porosity and thickness of the bed are not particularly critical and can be varied accordingly. As to nylon wool, it can be simply packed into a column or container of suitable size. The void volume of the nylon wool can be determined experimentally (i.e., trial and error).

For hollow fibers having pores in the wall, the size of the pores is not particularly critical. The cells are fed to the interior of the fibers and processed. The cells are stimulated with a tissue culture medium supplemented with a serum and a mitogen. The serum and mitogen are then forced through the pores in the wall. Thereafter, the cells are conditioned in the presence of a non-supplemented tissue culture medium. After conditioning, the tissue culture medium containing the product T-cell growth factor is flushed out of the interior of the fiber and concentrated to form the final product.

In the above description, it is mentioned that, upon conditioning for 12 to 20 hours under ordinary incubation conditions, the T-cell growth factor is released into the culture medium. The following procedure is used to determine the activity of the growth-factor-containing product.

Peripheral mononuclear blood cells are separated from the donor's blood. A cell count is conducted and the cells are incubated overnight in a tissue medium, e.g., RPMI 1640, without any supplements. By such soaking, serum protein and macrophage adhered to the surface of the cells becomes unattached. The cell density is adjusted to one million per ml of RPMI 1640.

The unconcentrated growth factor containing supernatant obtained after conditioning as previously described is deposited in the first row of a microtiter plate. The second row of wells contains a solution of the growth factor wherein its concentration is half of that of the first row. Similarly, the third row is half of that of the first row, etc. As a result, a microtiter plate is obtained wherein a dilution factor of the supernatant concentration of 1:2 is obtained as one moves from the top towards the bottom of the plate.

Figure 1:
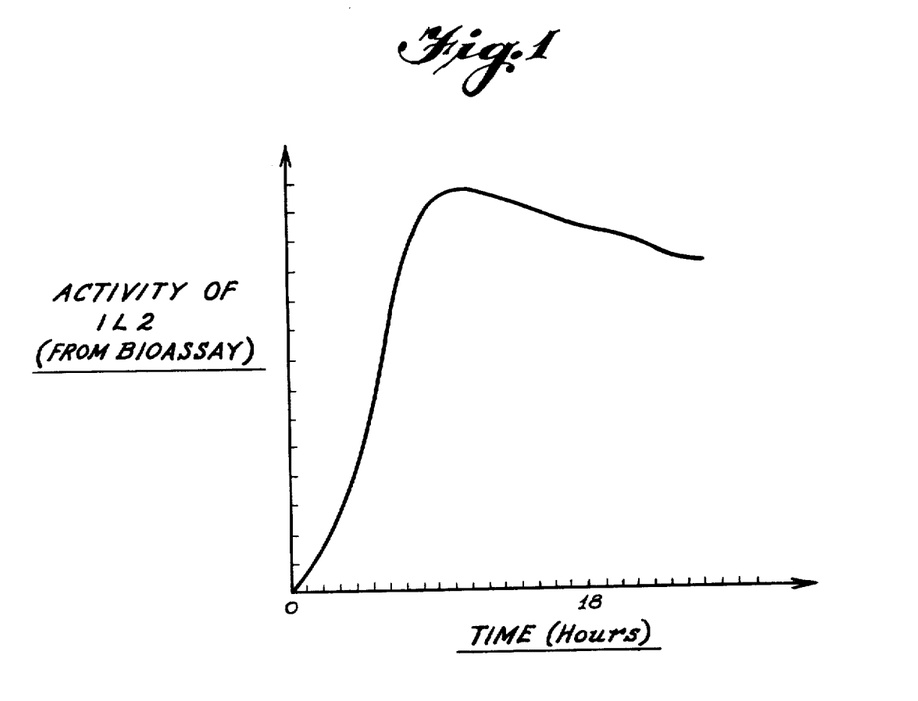
FIG. 1 shows the relation between IL 2 activity and conditioning time.

A measured number of the mononuclear cells which have been incubated overnight is added to each well in the microtiter plate. The growth of the cells as a result of stimulation by the T-cell growth factor is monitored. In order to define a reasonable standard of significant growth, the present inventors have adopted the inverse of dilution in which the cells double their density in seven days. By using such a standard, it has been found that significant growth is found in inverse of dilutions 4 to 32, most usually in 8 to 16. This standard is used in determining the relationship between T-cell growth factor activity and conditioning time shown in FIG. 1.

The above-described procedure is believed to yield measurements on T-cell growth factor (IL 2) rather than lymphocyte activating factor (LAF), also known as Interleukin 1 (IL 1). The reasons for such belief are as follows.

By definition, IL 1 is able to induce blast transformation of T-cells in serum but is incapable of maintaining T-cell lines. IL 1 is believed to be produced by the reaction between antigen and macrophage. As a second step, IL 1 reacts with the antigen and T-helper cells to produce IL 2. A detailed analysis of the mechanism of IL 1 and IL 2 production is presented by Wagner, et al., *Immunological Rev.*, Vol. 51, 215 (1980). Thus, in determining the effect of IL 2 (T-cell growth factor), precaution should be taken so that IL 1 production by the cells is stopped and only IL 2 is produced. The pre-incubation of the peripheral mononuclear cells for a period of at least 12 hours, preferably 12-18 hours is for the purpose of removing the macrophage or adherent cells from the mononuclear cells. The removal of the macrophage stops production of IL 1. As a result, cell growth resulting from contact between the pre-incubated mononucelar cells and the unconcentrated T-cell growth factor can be attributed only to IL 2. In the event that the mononuclear cells are not subjected to pre-incubation, upon contact with a mitogen the cells generate IL 1. When these cells are subsequently contacted with the T-cell growth factor, cell growth due to both IL 1 and IL 2 can result. Accordingly, the activities measured without pre-incubation are the result of two growth factors, which is obviously inaccurate.

The serum-free and mitogen-free T-cell growth factor of the present invention finds utility in numerous areas. It can be used in the diagnosis and treatment of immune deficiency in tumor patients. It has been found that patients suffering from tumors usually lack T-cell growth factor, i.e., they have a suppression in natural killer cell functions. By stimulating the patient with the present growth factor, the suppression of the natural killer cell function can be reversed or eliminated, thus leading to the killing of the tumor cells. In this connection, peripheral mononuclear cells can be collected from a patient and stimulated with the present T-cell growth factor. After sufficient cell growth, the cells are re-introduced into the patient to increase the patient's resistance to the tumor cells.

The present T-cell growth factor may also be used to produce specific immune responses by sensitizing a specific cell line or natural killer cell line against specific antigens. Such a cell line may then be used therapeutically to fight parasites and bacterial infection, e.g., tuberculosis and malaria. It has been shown that IL 2 producer cells are suppressed in tuberculosis patients. The suppression can be overcome by treating the patient with a cell line which has been specifically sensitized to act against tubercle bacillus.

On the other hand, T-cell growth factor has been shown to be capable of stimulating or improving natural killer cell function. By removing, or reducing this growth factor, the tendency for a patient to reject a transplanted organ can be controlled. It is the usual practice to administer to transplant patients immunosuppressive agents, e.g. cortisones, to prevent rejection of the transplanted organ. Cortisones act on the cellular immune system by killing macrophage which inhibits the production of both IL 1 and IL 2. However, it is desirable only to stop production of IL 2 which is a much more potent rejector of transplanted organs. To prevent rejection of the transplanted organ, serum-free IL 2 can be used as antigen to develop antibodies in animals. These antibodies can then be used to inhibit graft rejection.

The present invention is further illustrated by the following non-limiting examples:

EXAMPLE 1

Human blood contained in a one-pint plastic bag and mixed with a clotting inhibitor, Heparin, is obtained from a blood bank. Twenty 50 ml sterile tubes are prefilled with Ficoll-hypaque mixture. The blood is layered into the Ficoll-hypaque containing tubes. The tubes are centrifuged at 400 G for ten minutes. As a result of the centrifugation, a ring of the peripheral mononuclear blood cells is formed above the Ficoll-hypaque layer in each tube. This layer of the peripheral mononuclear blood cells is drawn off carefully by means of a pipet. The cells collected from ten tubes are deposited into one 50 ml tube, the amount of the cells added being approximately 25 ml. To this tube is added about 25 ml RPMI 1640 solution in order to dilute the concentration of the Ficoll-hypaque in the tube. Since Ficoll-hypaque is slightly toxic, it is separated from the cells carefully.

The tube containing the cells and RPMI 1640 is centrifuged for ten minutes at 300 G. The centrifugation forces are kept low in order to avoid unnecessary breakage of the cells. After centrifugation, the supernatant is discarded.

A fresh portion of RPMI solution is added to the tube. The cells are washed by resuspending the cells in the solution. Such resuspension is conducted by drawing the solution and cells into a pipet and then permitting the mixture to flow back into the tube. Once again, the suspension of the cells is conducted in a gentle manner in order to avoid breakage of the cells. The suspension is then centrifuged for ten minutes at 300 G to obtain a cell pellet and a supernatant which is discarded. This washing procedure is repeated for a total of three times, with the supernatant obtained in each washing being discarded and the cell pellet being retained. After washing, the cells are suspended in 5 to 10 ml RPMI 1640 solution and counted. Usually, the blood contains 500–1,000 million cells.

A stock solution of phytohemagglutinin (PHA) (highly purified, Wellcome) is added to RPMI 1640 solution supplemented with 15% v/v AB human serum to form a solution containing four micrograms PHA per ml supplemented RPMI 1640. The so-obtained RPMI 1640 solution is added to the cells, the volume of the RPMI 1640 added being adjusted so that a cell density of 10 million per ml supplemented RPMI 1640 solution is obtained. The cell/solution mixture is deposited into 50 ml tubes which are then placed in an incubator (National Incubator Company) for four hours. The incubator is maintained at 37° C., a humidity of 98% in an atmosphere containing 7.5% $CO_2$.

After incubation, the tubes are removed from the incubator and centrifuged at 300 G for ten minutes at room temperature. The supernatant is decanted and saved for later use. A fresh portion of RPMI 1640 which contains no serum and no PHA is introduced into the tube to about the 30 ml mark. The cells are resuspended and washed. Thereafter, the suspension is subjected to separation by centrifugation. This washing, suspending and separation step is repeated three times, each time with a fresh portion of serum- and PHA-free RPMI 1640 solution. It is estimated that by washing the cell pellet three times, the concentration of the serum is diluted by a factor of about $3 \times 10^7$.

After the last washing, the suspension which has a cell density of $3 \times 10^6$/ml is not subjected to centrifugation. Instead, the suspension is placed in the incubator and incubated for 18 hours. After 18 hours, the suspension is centrifuged at 300 G for 10 minutes. The supernatant is decanted and saved. The cell pellet is resuspended in the PHA and serum-containing supernatant which has been saved after the first incubation (stimulation) step. The procedure for stimulating (incubating the cells in the presence of a supplemented RPMI 1640 solution) and conditioning (incubating the cells in the presence of a serum and PHA-free RPMI 1640 solution) is repeated. It has been found that the same batch of cells can be restimulated and reconditioned for up to five times.

The supernatant collected after the conditioning (i.e., second incubation step) is filtered through a sterile filter having a porosity of 0.2–0.4 microns. This filtration step is necessary since cells may clog the ultrafilter used in concentrating the supernatant. The filtered supernatant is then frozen and stored at −20° C. Concentration of the supernatant is usually conducted after several batches of the supernatant have been collected since, in each test run, the amount of supernatant collected is small.

To concentrate the supernatant, an ultrafilter in a thin channel system is used. Such an ultrafilter is made by the Amicon Company, U.S.A. The filter membrane used is either YM-10 or YM-30. These membranes are used because they do not absorb protein. The product is retained on top of the membrane. As a result of the concentration step, the supernatant is concentrated about 50 to 100 times.

Regarding the concentration step, activities have been found in the supernatant prior to concentration between dilution portions 2 and 16. Accordingly, if the supernatant is concentrated 50 times, the concentrate can be diluted by a dilution factor ranging between 100 and 800 and still provide "significant growth."

The concentrated supernatant is frozen at −20° C. and can be stored for more than one year without affecting its biological activity.

In general, a one-pint bag of blood yields approximately 1,000 to 1,200 ml of supernatant before concentration. After concentration, about 25 ml of supernatant is usually obtained.

EXAMPLE 2

Peripheral mononuclear blood cells are isolated and washed three times with RPMI 1640 in accordance with the procedure described in the Example 1. After washing, the cells are ready for adhering to a substrate. In this example, glass beads having diameters ranging from 50 to 100 microns are stored in a glass column, which is 50 mm in diameter and 300 mm in length. The diameter and length of the column may vary between 20 and 50 mm and 200 and 300 mm, respectively. The washed peripheral mononuclear blood cells suspended in RPMI 1640 are poured into the column, with flow out of the column being stopped in order to allow the cells to adhere to the glass surface. Since the adhering process is a slow one, one hour is allowed for such adhering. Thereafter, the entire column is incubated for one hour at 37° C.

Fresh RPMI 1640 solution is then fed to the column to flush out non-adhering cells. The amount of RPMI 1640 solution used is about two volumes of the column. In this connection, the amount of RPMI 1640 added to the column is equal to the amount removed at the bottom of the column so that the column is always filled. After the entire amount of RPMI 1640 solution has been added to the column, the solution is permitted to drain completely from the column. Thereafter, flow out of the bottom of the column is stopped. The cells are now ready for stimulation.

To stimulate the cells, the column is filled with RPMI 1640 solution supplemented with 15% human AB serum and four micrograms PHA/ml of the RPMI 1640 solution. The column is then sealed and subjected to incubation under the usual conditions used in tissue culture, i.e., 37° C. and 7.5% $CO_2$ atmosphere. The column is incubated for four hours. The supplemented RPMI 1640 solution is then drained out of the column and collected for later use. The cells in the column are washed with two column volumes of RPMI 1640 containing no supplements. Once again, fresh RPMI 1640 is added to the top of the column whereas "used" RPMI 1640 is removed from the bottom, the flow rates of the two streams being so adjusted that the column is always filled with the solution. After the two column volumes of the RPMI 1640 solution have been added to the column, the solution is permitted to drain out of the column. The cells are now ready for conditioning.

To condition the cells, the column is filled with a fresh portion of RPMI 1640 and sealed. The column is then incubated for 18 hours under the usual incubation conditions. Thereafter, the RPMI 1640 solution containing the product growth factor is drained out of the column. Fresh portions of RPMI 1640 are then added to the column to remove as much of the growth factor as possible. The so-collected portions of RPMI 1640 solution is then subjected to concentration. On the other hand, the cells in the column are now ready for another cycle of stimulation and conditioning.

This example shows a continuous batchwise process to produce the T-cell growth factor of the present invention.

EXAMPLE 3

The procedure outlined in Example 2 is repeated with the exception that the column filled with glass beads is replaced by a funnel having a layer of fritted glass as a filter.

EXAMPLE 4

The spleen is removed from a human donor under aseptic conditions. The spleen is cut into small pieces, each weighing about 0.2 to 0.4 grams. The cut spleen is placed between two stainless steel meshes, each having a mesh size of about 0.1 mm. The screens are gently brought together, the spleen being simultaneously flushed with a sterile saline solution to yield a porage-like produce which contains the mononuclear cells. The so-obtained product is layered onto Ficoll-hypaque gradients to extract the mononuclear cells and T-cell growth factor in accordance with the procedure outlined in Example 1.

EXAMPLE 5

This example is directed to the bioassay used in determining the significant growth of the T-cell factor obtained in the present invention. Peripheral mononuclear blood cells are isolated in accordance with the procedure outlined in Example 1. The cells are then counted and dispersed in RPMI 1640 solution without any supplements for a period of about 18 hours. As a result, serum proteins and macrophage adhered to the cell surfaces become unattached. Fresh RPMI 1640 is added to the suspension after soaking in order to adjust the cell density to one million/ml. A microtiter plate having eight rows of wells in one direction and twelve in the other direction is used to conduct the bioassay. For each well, the maximum filling volume is 250 microliters. 200 microliters of the product supernatant obtained in Example 1 are deposited into the first row of the microtiter plate. In the second row, 100 microliters of the product supernatant are deposited together with 100 microliters of RPMI 1640 containing no supplements. Thus, a dilution factor of 1:2 is obtained between the first and second rows. In the third row, the concentration of the supernatant is equal to half of that in row 2. Similarly, the remainder of the rows of wells in the plate is filled with RPMI 1640 solution so that the concentration of the T-cell growth factor in one row is half of that in the previous row.

50 microliters of the peripheral mononuclear blood cells which have been incubated overnight are placed into each well. The cells are permitted to grow for a period of seven days. The cells start to grow as a result of stimulation by the T-cell growth factor contained in each well. Two sets of tests are made in order to obtain an average value for the experiments.

Significant growth, as defined above, is found in portions or titers 4–32.

The strength of each batch of T-cell growth factor obtained may be compared to known stock of the growth factor used as a control. When using the present growth factor for therapeutic purposes, it would be necessary to determine the strength of the product, i.e., which titer contains acceptable activity.

EXAMPLE 6

This example is directed to the determination of the suppression of T-cell growth factor in patients suffering from tumors.

A blood cell sample is withdrawn from a patient and 200,000 peripheral mononuclear blood cells are isolated therefrom. The cells are mixed with soft agar and RPMI 1640 supplemented with 15% v/v of human AB serum and 4 micrograms PHA/ml RPMI 1640. The mixture is then incubated under the usual tissue culture conditions for a period of seven to nine days.

As a result of stimulation by the PHA, T-cell growth factor begins to produce and start colonies of natural killer cells on the surface of agar, which colonies take the form of patches. As a quantitation, the number of colonies on the agar surface is counted and based on the number of cells fed. In this connection, by colony it is meant a patch containing more than 50 cells. For healthy patients, i.e., patients not suffering from tumors, 1,000 to 1,500 colonies should be obtained.

Figure 2:
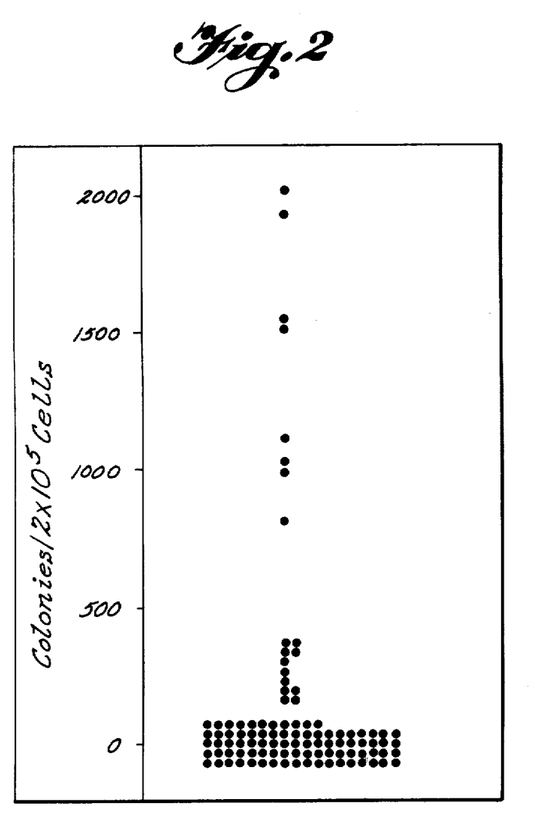
FIG. 2 summarizes the results obtained in T-cell colony growth in response to in vitro PHA stimulation of blood cells from tumor patients.

Similar assays are conducted on other patients known to be suffering from tumors. The results are summarized in Table 1 and presented graphically in FIG. 2. The results show that only 6 out of 71 patients tested gave false negatives, i.e., their results appear normal.

TABLE 1

| Type of tumor | No. of patients with less than 1,000 colonies | No. of patients with more than 1,000 colonies | % of total patients |
|---|---|---|---|
| Bronchial carcinoma | 10 | 2 | 17 |
| Mammary and genital carcinoma | 9 | 2 | 16 |
| Hodgkin's disease | 9 | 0 | 13 |
| Acute leukemia | 8 | 0 | 11 |
| N.H. lymphomia | 6 | 1 | 10 |
| Melanoma | 5 | 1 | 8 |
| carcinoma of the oral cavity | 5 | 0 | 6 |
| Chronic leukemia | 3 | 0 | 5 |
| gastrointestinal carcinoma | 2 | 0 | 3 |
| various | 8 | 0 | 11 |
| Total | 65 | 6 | 100 |

Figure 3:
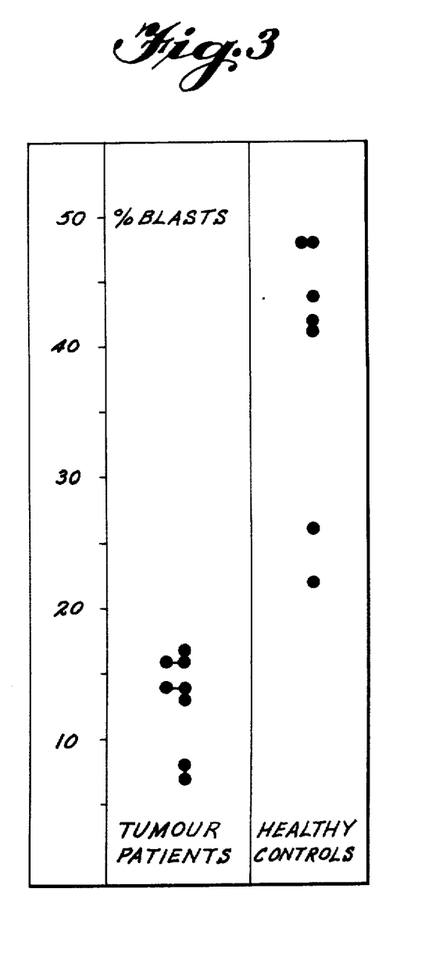
FIG. 3 shows a comparison of IL 2 production in blood cells from tumor patients and healthy patients.

As a comparison, the above procedure is applied to cells taken from healthy patients. The assay data obtained from healthy and tumor patients are shown in FIG. 3 which demonstrates that the production of IL 2 is suppressed in peripheral blood cells from tumor patients.

The test procedure outlined above represents a highly definitive test for determining whether a person is suffering from tumor.

EXAMPLE 7

The experiments in this example are conducted to show that co-cultivation of blood cells from tumor patients with those from healthy donors results in a suppression of the colony growth of the T-cells from healthy donors.

Peripheral mononuclear blood cells are isolated from blood samples taken from tumor patients. The method of isolation of the cells is identical to that illustrated in Example 1. The cell samples are individually mixed with soft agar and RPMI 1640 supplemented with serum and PHA as outlined in Example 6, after which the mixtures are incubated. The cells so obtained represent batch A.

Cells from healthy donors are stimulated using the method shown in the preceeding paragraph. The so-obtained cells represent batch B.

Figure 4:
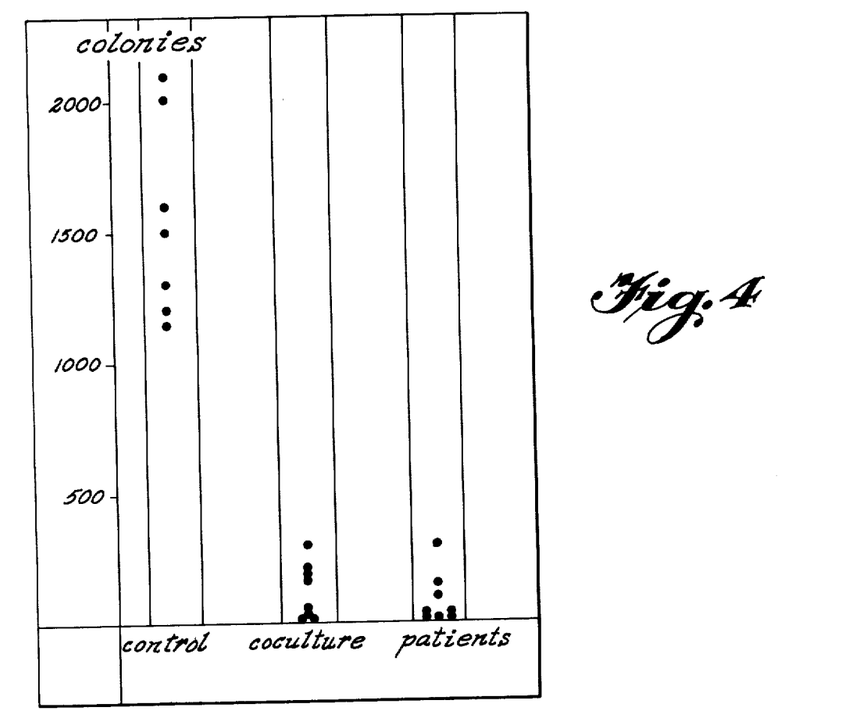
FIG. 4 illustrates the results from colony growth of T-cells from tumor patients, healthy patients and mixed T-cells from healthy and tumor patients.

A third batch of cells, batch C, is obtained by mixing samples from batches A and B and incubating the mixture in the presence of soft agar and RPMI 1640 supplemented with serum and PHA. The results obtained for batches A,B and C are illustrated in FIG. 4. The results show that co-cultivation of blood cells from healthy donors and tumor patients lead to a suppression of T-cell colony growth.

EXAMPLE 8

The experiments in this example are conducted to show that the serum-free and mitogen-free T-cell growth factor of the present invention can be used to increase in vitro natural killer cell production in tumor patients.

Peripheral mononuclear blood cells are isolated from a blood sample taken from a tumor patient. The procedure for the isolation is identical to that shown in Example 1. The cells are added to a culture system comprising 1.25 ml hard agar, 0.2 ml soft agar, and 0.05 ml of a concentrated T-cell growth factor obtained as in Example 1. The culture system is incubated for seven days under the usual tissue culture conditions. The growth of natural killer cells as evidenced by the formation of colonies on the agar surface is noted.

As a control experiment, another sample of the isolated peripheral mononuclear blood cells taken from the same patient is added to a culture system comprising 1.25 ml hard agar, 0.2 ml soft agar and 0.05 ml RPMI 1640. This culture system is incubated for seven days under the usual tissue culture conditions. In both the control and test procedures, a cell density of 200,000/ml is used.

Figure 5:
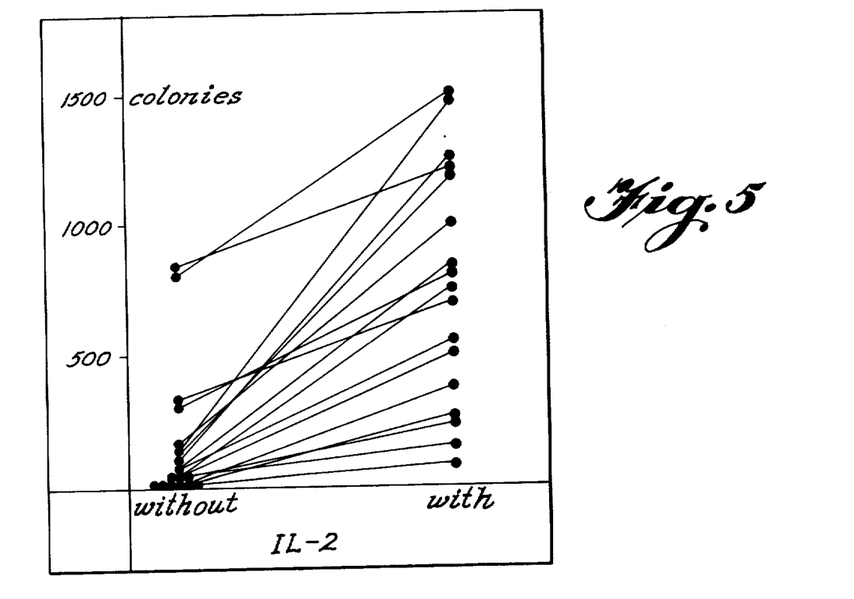
FIG. 5 summarizes the results obtained in T-cell colony growth of blood cells from tumor patients with and without IL 2.

The above-described experiment is repeated for numerous patients. The results obtained from these experiments are summarized in FIG. 5 wherein the straight lines connect the number of colonies obtained with and without the present T-cell growth factor for one particular patient. The results clearly show that treatment with the present T-cell growth factor clearly enhances the growth of T-cell colonies, i.e., an increase in the production of natural killer cells.

EXAMPLE 9

The following tests are conducted to determine the tumorcell killing capability of T-cell growth factor. Tumor cells from HeLa strain is labelled with $^{51}Cr$. The cells are washed and coincubated with toxic lymphoblasts for 18 hours. The supernatant is decanted and the cells are centrifuged. The release of $^{51}Cr$ from the target (or labelled) tumor cells indicates that the cells have been killed. The results are summarized in Table 2.

TABLE 2

| | % of $^{51}Cr$ Released | | |
|---|---|---|---|
| | Target and T-cell | Target and HeLa-control | Target and TCGF-containing culture medium |
| Test 1 | 82.4 | 2.9 | 0 |
| Test 2 | 88.8 | 23.4 | 0 |

EXAMPLE 10

This example illustrates that no toxic substances, such as lectins, are present in the T-cell growth factor of the present invention.

Tests are conducted in ten rats. Into each rat, 15 ml of 50 fold concentrate of the T-cell growth factor obtained in Example 1 is injected. The effects of the T-cell growth factor on the rats are observed. After four weeks, nine of the rats are sacrificed and their bodies examined. No adverse effects due to the presence of toxic substances are found in the lymph nodes in these rats. The tenth rat showed no ill effects from the injection even after six months.

We claim:

1. A process for producing a serum-free and mitogen-free T-cell growth factor comprising:
   (1) separating peripheral mononuclear blood cell from a donor;
   (2) stimulating the cells by incubating the cells in a liquid tissue culture medium supplemented with serum and a mitogen;
   (3) separating and washing the stimulated cells to remove substantially all of the serum and mitogen; and
   (4) conditioning the cells obtained in step (3) by incubating the cells in the presence of a serum-free and mitogen-free liquid tissue culture medium to thereby transfer the T-cell growth factor into the liquid phase.

2. A process for producing a serum-free and mitogen-free T-cell growth factor comprising:
   (1) separating peripheral mononuclear blood cells from a donor;
   (2) washing the cells several times with a liquid tissue culture medium;
   (3) separating the washed cells from the tissue culture medium;
   (4) stimulating the cells obtained in step (3) by incubating the cells in a tissue culture medium supplemented with serum and mitogen;
   (5) separating the stimulated cells from the medium;
   (6) washing the stimulated cells with fresh tissue culture medium several times to remove substantially all of the serum and mitogen;
   (7) suspending the cells obtained in step (6) in another portion of fresh tissue culture medium;
   (8) conditioning the cells in the suspension of step (7) by incubating cells so as to transfer the growth factor into the liquid; and
   (9) separating the conditioned cells from the solution to obtain a supernatant containing the growth factor.

3. The process of claim 2 wherein in the stimulating step, the liquid tissue culture medium comprises RPMI 1640 supplemented with 15% vol/vol human AB serum and phytohemagglutinin as the mitogen which is present in an amount of about 4 micrograms per ml of the medium.

4. The process of claim 2 wherein in the stimulation step the incubation is conducted at a temperature of 37° C. in an atmosphere containing 5–10% $CO_2$ for a period of 4 to 12 hours.

5. The process of claim 2 or claim 4 wherein in the conditioning step the incubation is conducted at a temperature of 37° C. for a period of 12 to 24 hours in an atmosphere containing 5–10% $CO_2$.

6. The process of claim 2 including the additional steps of filtering and concentrating the product supernatant by a factor ranging from 50 to 250.

7. The process of claim 2 wherein the donor in step (1) is selected from the group consisting of cattle, pigs, sheep, and humans.

8. The process of claim 2 wherein the mononuclear blood cells are separated from the blood or spleen of the donor.

9. The process of claim 2 wherein the serum used in the stimulation step is human AB serum.

10. The process of claim 2 wherein the liquid tissue culture medium is RPMI 1640.

11. The process of claim 2 wherein in steps (3), (5) and (9), the separation comprises centrifuging for 10 minutes at 300 G.

12. The process of claim 2 wherein the liquid tissue culture medium from which the stimulated cells were separated in step (5) is recycled to stimulate subsequent batches of cells.

13. The process of claim 2 wherein the conditioned cells obtained in step (9) are recycled to step (4) for restimulation.

* * * * *